Figure 1:
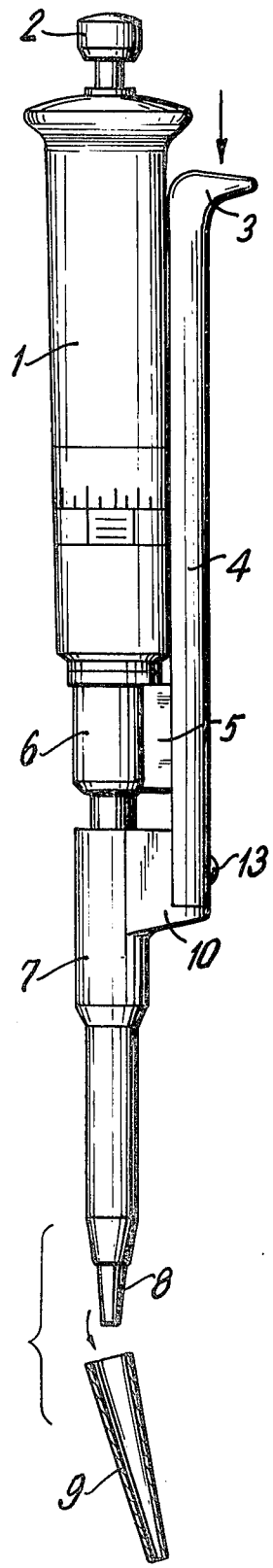

United States Patent [19]

Suovaniemi et al.

[11] 4,151,750

[45] May 1, 1979

[54] DEVICE FOR DETACHING AND REMOVING A DISPOSABLE TIP OF A PIPETTE

[75] Inventors: Osmo A. Suovaniemi; Jukka Tervamaki, both of Helsinki, Finland

[73] Assignee: Kommandiittiyhtio Finnpipette Osmo A. Suovaniemi, Helsinki, Finland

[21] Appl. No.: 875,097

[22] Filed: Feb. 3, 1978

[30] Foreign Application Priority Data

Feb. 17, 1977 [FI] Finland .................................. 770510

[51] Int. Cl.² .............................................. B01L 3/02
[52] U.S. Cl. ................................................ 73/425.6
[58] Field of Search .................... 73/425.4 P, 425.6

[56] References Cited

U.S. PATENT DOCUMENTS

| | | | |
|---|---|---|---|
| 3,991,617 | 11/1976 | D'Autry | 73/425.4 P |
| 4,054,062 | 10/1977 | Branham | 73/425.6 |

Primary Examiner—S. Clement Swisher

Attorney, Agent, or Firm—Francis J. Murphy

[57] ABSTRACT

A device is disclosed for removing a disposable tip from a pipette. The device includes an elongated shaft with a flattened push-button at one end and an elongated groove. Elongated projections extend inwardly from each side of the groove.

A guide member extends outwardly from the pipette. The guide member includes opposed longitudinal notches configured to mate with the projections along the sides of the groove in the shaft and includes an end portion configured to slide within the groove in the shaft.

A sleeve is attached to the second end of the shaft. The sleeve is configured to slide over the exterior surface of the pipette. A spring is disposed within the shaft groove and biases the shaft and attached sleeve into a first position where the end of the pipette is exposed so that a disposable tip can be attached to it. When the push-button is depressed, the shaft and sleeve move downwardly along the pipette to push off the disposable tip.

8 Claims, 6 Drawing Figures

U.S. Patent   May 1, 1979   Sheet 1 of 3   4,151,750

DEVICE FOR DETACHING AND REMOVING A DISPOSABLE TIP OF A PIPETTE

The subject of the present invention is a device for detaching and removing a removable mouth-piece or disposable tip of a pipette, which device comprises a shaft whose upper end is provided with a press button and whose lower end is connected with a sleeve-shaped pushing means placed around the tubular lower portion of the pipette, which pushing means can, together with the shaft, move as parallel to the longitudinal axis of the pipette when the button is pressed with the finger downwards and which shaft and pushing means can be restored to their initial positions by means of a spring.

By means of the device subject of the invention, it is possible to detach and remove the removable mouth-piece or so-called disposable tip of a pipette hygienically, untouched by hand. It is a previously known procedure to provide the tubular lower end of pipettes, especially of precision-micropipettes, with a removable tip, which is usually made conical in order to provide good fastening. By means of detachability and removability of the mouth-piece, the risk of contamination of the pipette itself is avoided, as the liquid is sucked only into the mouth-piece, which can be replaced by a new one if the next sample requires that. In the Finnish Patent No. 47,461 a pipette type of this sort is described, in which replaceable mouth-pieces are used and whose pipetting volume is, in the case described in the patent, additionally adjustable.

Since such pipettes are frequently used for the dosage of highly active chemical and biological samples and reagents, it is quite desirable that the detaching and removal of the tip should not have to be performed by touching the tip by hand.

Several methods and devices are previously known for the removal of the tip untouched by hand. E.g., the waste box into which the discarded tips are removed may be provided with a U-shaped notch, against which the pipette can be pulled so that the tip is detached and falls into the box. Devices are also known which, themselves mounted on the pipette, function as tip removers when the operating button of the device concerned is pulled, turned or pushed either by one hand or by two hands. Said tip-removing devices are, however, often of quite a complicated construction and consist of several components and they require considerable additions and expensive constructional details in the pipette itself right at the manufacturing stage.

It is an object of the present invention to provide a tip-removing device that is of a simple construction and in which the drawbacks previously encountered in corresponding devices are eliminated.

The device in accordance with the invention is characterized in that the shaft of the device for the removal of disposable pipette tip is placed outside the pipette body and pipette handle and that the movement of the shaft and of the pusher means is most appropriately supported and guided longitudinally by means of a guide means connected to the lower portion or handle of the pipette so that the shaft and the guide means are fitted together by means of a groove joint, furrow joint or any other joint suitable for the purpose, which joint permits the shaft to move in relation to the guide means in the direction of the longitudinal axis of the pipette.

Figure 2:
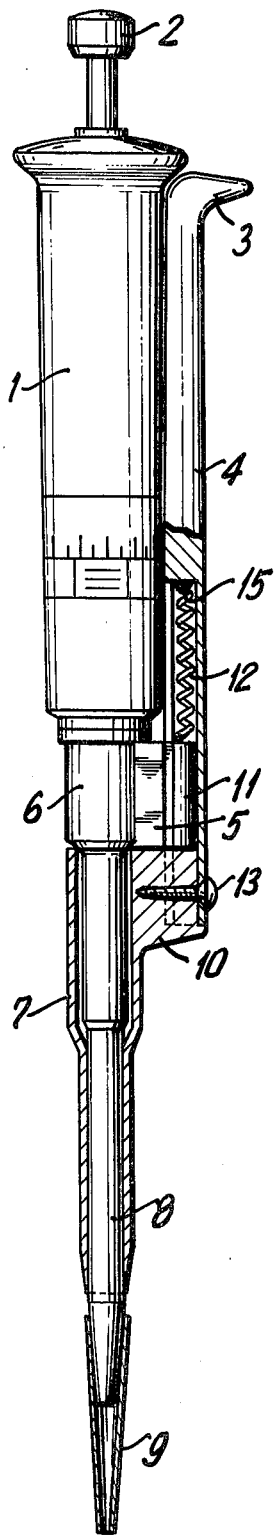
Figure 3:
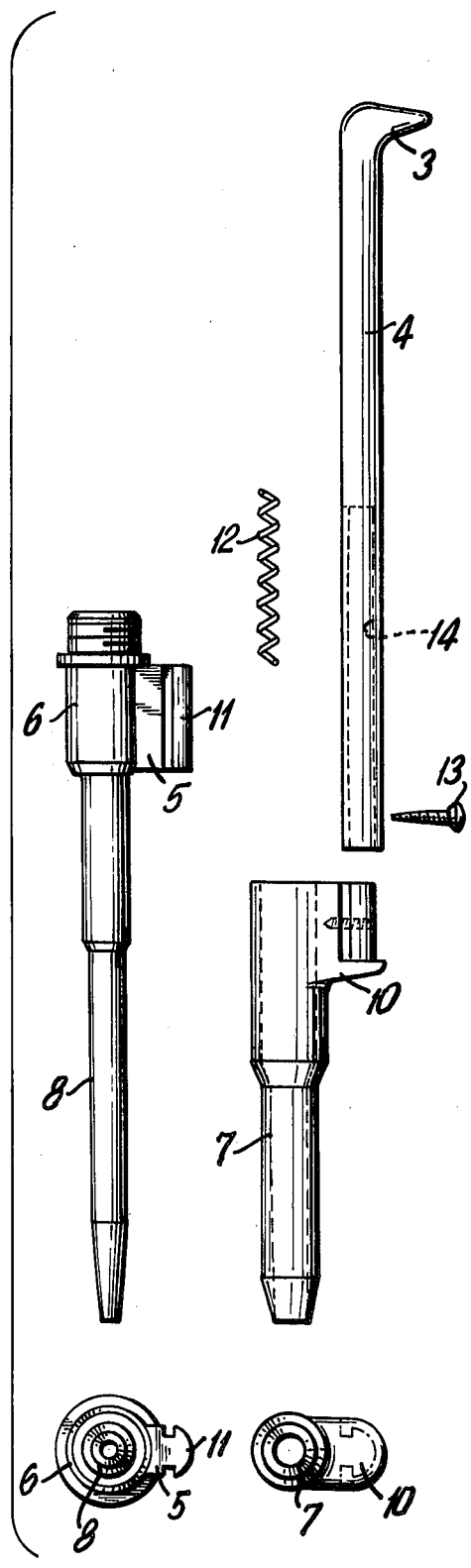
Figure 4:
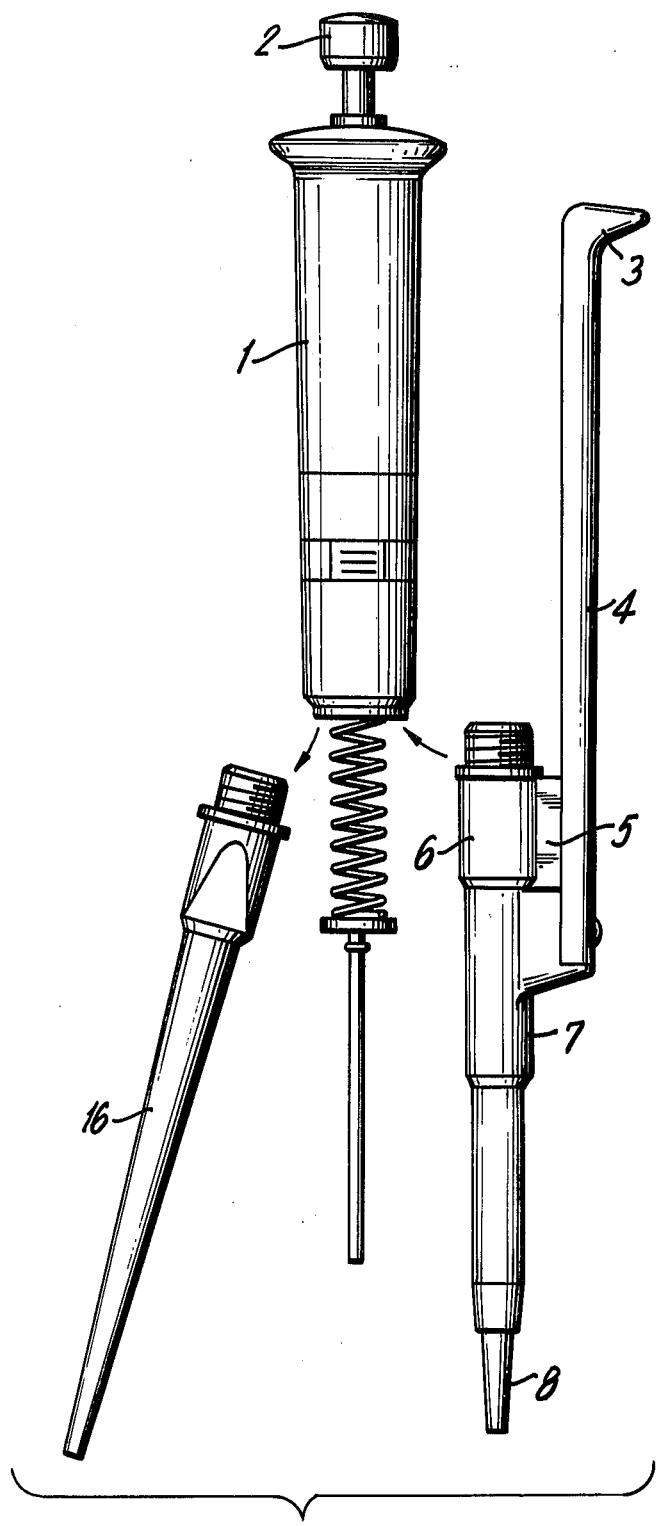
Figure 5:
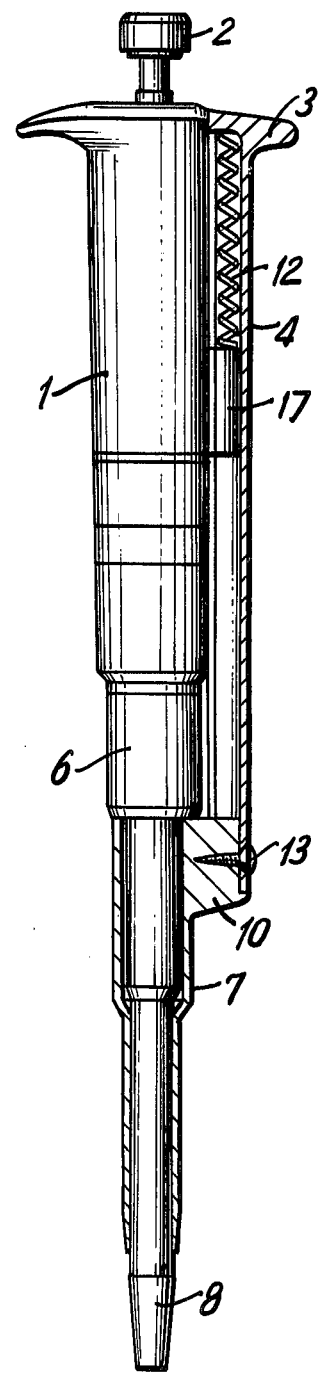
Figure 6:
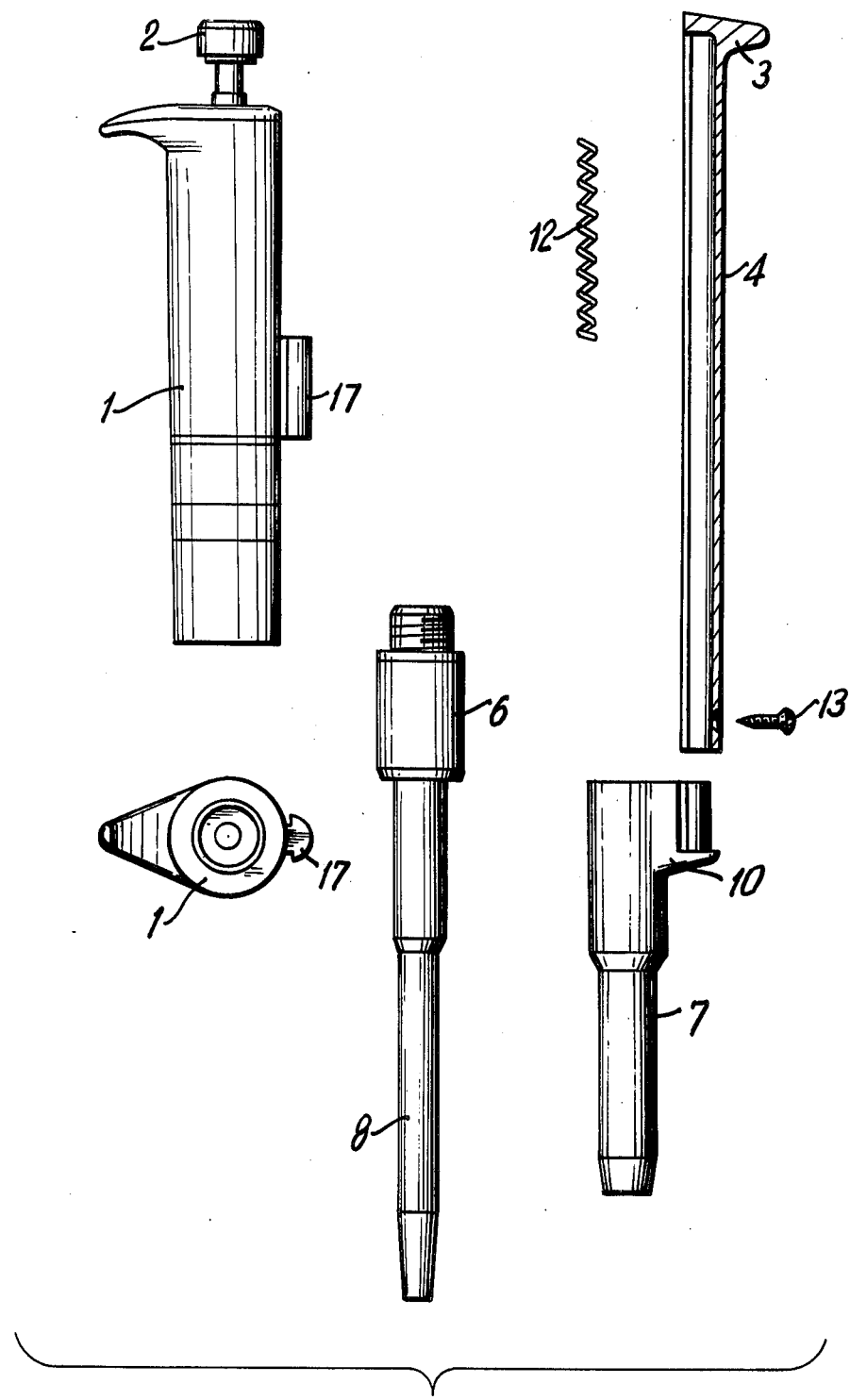

The invention comes out more closely from the following description and from the attached drawings, wherein FIG. 1 is a side view of a pipette provided with a tip remover in accordance with the present invention, FIG. 2 is also a side view of the pipette shown in FIG. 1, but presented partly in section, FIG. 3 is an exploded view of the lower portion of the pipette and of components related to the tip remover, FIG. 4 shows a favourable embodiment of the device in accordance with the invention, in which embodiment the device concerned can be afterwards mounted on pipettes of the same manufacture, FIG. 5 shows an embodiment alternative to the embodiment shown in FIGS. 1 to 3, in which embodiment the guide means for the shaft is fastened to the handle of the pipette, and FIG. 6 shows an exploded view of the exemplifying embodiment shown in FIG. 5.

FIG. 1 illustrates the operation of the tip remover in accordance with the invention. The operation of such a pipette in liquid dosage is previously known, e.g., on the basis of the Finnish Patent No. 47,461. The liquid dosage is performed by using the button 2 at the top end of the pipette 1, by means of which button the liquid to be pipetted can be made to rise into a disposable container 9, and also to come out from said container.

In the device in accordance with the invention, the removal of the disposable container 9 takes place by hereupon pressing the button 3 at the side of the pipette handle 1, which button, by means of a shaft 4 placed outside the handle 1 as parallel to same, transfers the movement to the sleeve-shaped pusher means 7, which moves around the tubular lower portion 8 of the pipette in the direction of the longitudinal axis of the pipette and is pressed against the disposable tip 9 and detaches said tip from its friction joint on the tubular lower portion 8 without the tip 9 being touched by hand.

FIGS. 2 and 3 show the construction and components of the tip remover in accordance with the invention in a particular embodiment of same.

The shaft 4 of the tip remover is placed outside the body and handle 1 of the pipette parallel to the longitudinal axis of the pipette. The upper end of the shaft 4 has a button 3 appropriately shaped for the finger tip, and the lower end of the shaft 4 is fastened by means of a screw 13 to a means 10 at the upper end of the sleeve-shaped pusher means 7. The joint between the shaft 4 and the fastening means 10 can, in stead of the groove-T-joint and screw 13 shown in the figure, also be of any other type, e.g. plane faces glued to each other or a friction joint. It is also possible to manufacture the button 3, the shaft 4, and the pusher means 7 as one piece, e.g., out of plastics.

In order to guide the movement of the shaft 4 and of the pusher means 7, it is possible to provide the tubular lower portion 6 of the pipette with a guide means 11 on which the shaft 4 can glide as parallel to the longitudinal axis of the pipette. From the point of view of operation of the invention, the guide 11 is, however, not necessary, for the lower end 8 of the tubular lower portion 6 also provides the longitudinal movement with guidance.

For the purpose of restoring the pusher means 7 and the shaft 4 to their initial positions, the tip remover in accordance with the invention is provided with a spring 12, which is preferably placed in a groove 14 inside the shaft 4. The spring 12 may be either a pulling spring, or a pushing spring, as shown in FIGS. 2, 3, and 4, resting against a shoulder 15 in the shaft 4 and at the other end against the means 11. The movement of the pusher means 7 upwards is limited by a shoulder in the tubular lower portion 6.

It is characteristic of the tip remover in accordance with the present invention that it can be mounted on pipettes of the same manufacture already in use. It can be seen from FIG. 4 that by replacing the former lower portion 16 of the pipette by a new combination of parts 3, 4, 5, 6, and 7, it is possible to obtain a pipette provided with tip remover as shown in FIGS. 1 and 2.

FIGS. 5 and 6 show the invention in another possible embodiment of same, wherein the guide means 17 for the shaft 4 is fixed to the pipette handle. The spring 12 is placed inside the shaft 4 and lies against a shoulder in the button 3 and against the means 17 in the handle 1.

The embodiments of the device in accordance with the present invention are by no means restricted to the examples described above, but their combinations as well as other embodiments are numerous with the nature of the invention remaining the same. It should be noticed that the operator of a pipette provided with a tip remover in accordance with the present invention can perform the pipettings, sample-takings, and tip-removal advantageously by one hand, whereas the other hand remains free to perform liftings of test tubes or other operations. Of course, the device in accordance with the invention is equally well suitable for use by right-handed and left-handed people.

What we claim is:

1. A device for detaching a disposable tip from the body of a pipette, said pipette body having a longitudinal axis and including a handle portion and an elongated tubular dispenser attached to said handle portion, said device including:
   an elongated shaft disposed adjacent to the outer surface of the handle portion of the pipette substantially parallel to the longitudinal axis of the pipette, said shaft having a first and second end, an elongated longitudinal groove formed in a portion of said shaft surface adjacent to said pipette, said shaft including projections extending inwardly from each of the longitudinal sides of said groove;
   a guide member attached to and extending transversely outwardly from said pipette, said guide member having longitudinal slots formed in opposed sides, said slots being configured to mate with said projections along the longitudinal sides of the groove in said shaft and an end portion extending outwardly beyond said slots, said end portion being configured to slide within said groove in said shaft;
   a sleeve member configured to fit over said tubular dispenser portion of said pipette, said sleeve member being attached to said second end of shaft at a point below said groove; and
   bias means to bias said shaft and said attached sleeve member into a first predetermined position in which the lower portion of said tubular dispenser extends beyond said sleeve member, a disposable tip being attachable to said exposed portion of said tubular dispenser.

2. A device as claimed in claim 1 in which said bias means includes a spring disposed within the groove in said shaft between the end portion of said guide member and one end of said groove.

3. A device as claimed in claim 1 in which said tubular dispenser portion of said pipette includes a transversely projecting surface which abuts with said sleeve member when said sleeve member is in said first predetermined position.

4. A device as claimed in claim 1 in which said shaft includes a transverse flattened portion adjacent to said first end which is adapted to act as a push-button.

5. A device as claimed in claim 1 in which said guide member extends outwardly from the portion of said tubular dispenser adjacent to said handle portion and said shaft has said elongated groove formed adjacent to its second end.

6. A device as claimed in claim 1 in which said guide member extends outwardly from said handle portion of said pipette and said shaft has said elongated groove formed adjacent to its first end.

7. A device as claimed in claim 1 in which the sleeve member includes a transversely projecting portion and said projecting portion includes two opposed longitudinal slots configured to mate with said projections along the longitudinal sides of the groove in said shaft and having an end portion configured to fit slidably within the groove in said slot and in which said projecting portion further includes a transversely extending support surface which supports the second end of said shaft.

8. A device as claimed in claim 7 including fastening means to attach said shaft to said projecting portion of said sleeve member.

* * * * *